(12) United States Patent
Zhang et al.

(10) Patent No.: US 9,051,254 B2
(45) Date of Patent: Jun. 9, 2015

(54) METHOD OF PREPARING 2,6,10-TRIMETHYL-1,1-DIALKOXY-3,5,9-UNDECATRIENE USED AS AN INTERMEDIATE OF LYCOPENE

(75) Inventors: Pengfei Zhang, Zhejiang (CN); Chao Shen, Zhejiang (CN); Runpu Shen, Zhejiang (CN); Wei Liu, Zhejiang (CN); Chunlei Wu, Zhejiang (CN)

(73) Assignees: HANGZHOU NORMAL UNIVERSITY, Hangzhou, Zhejiang Province (CN); UNIVERSITY OF SHAOXING, Shaoxing, Zhejiang Province (CN)

( * ) Notice: Subject to any disclaimer, the term of this patent is extended or adjusted under 35 U.S.C. 154(b) by 400 days.

(21) Appl. No.: 13/493,971

(22) Filed: Jun. 11, 2012

(65) Prior Publication Data
US 2012/0316366 A1 Dec. 13, 2012

(30) Foreign Application Priority Data

Jun. 13, 2011 (CN) .......................... 2011 1 0157489

(51) Int. Cl.
*C07C 41/01* (2006.01)
*C07C 41/48* (2006.01)
(52) U.S. Cl.
CPC ..................................... *C07C 41/48* (2013.01)
(58) Field of Classification Search
CPC ..................................................... C07C 41/48
USPC .......................................................... 568/596
See application file for complete search history.

(56) References Cited

PUBLICATIONS

Faming Zhuanli Shenqing, Nov. 23, 2011, CASREACT abstract.*
Shen et al., "A novel and practical synthetic route for the total synthesis of lycopene", Tetrahedron, 67, May 2011, pp. 5610-5614.*

* cited by examiner

*Primary Examiner* — Rosalynd Keys
(74) *Attorney, Agent, or Firm* — Tianhua Gu; Global IP Services

(57) ABSTRACT

The present invention describes a novel synthetic method for preparing the key intermediate 2,6,10-trimethyl-1,1-dialkoxy-3,5,9-undecatriene of lycopene. An existing synthetic method have some disadvantages that it is very difficult to gain the raw material dialkyl 4-methyl-5,5-diakoxy-1-pentene-1-phosphonate (10) because no effective synthetic method can be adopted, and furthermore the obtained target compound is composed of several cis/trans isomers. This invention relates to a process comprising a condensation step wherein a starting C10-phosphonate is changed to its carbanion completely at a temperature of −40~30 under an atmosphere of a non-reactive gas in an organic solvent catalyzed by base, and then C4-dialkyl is added to undergo Wittig-Horner condensation. This invention affords all trans C14-acetal and this method is characterized with the advantages of simple procedure, easy access to raw material and low cost, which makes it has the value of industrial application.

10 Claims, No Drawings

METHOD OF PREPARING 2,6,10-TRIMETHYL-1,1-DIALKOXY-3,5,9-UNDECATRIENE USED AS AN INTERMEDIATE OF LYCOPENE

CROSS REFERENCE TO RELATED PATENT APPLICATION

The present application claims the priority of the Chinese patent application No. CN201110157489.X filed on Jun. 13, 2011, which application is incorporated herein by reference.

BACKGROUND OF THE INVENTION

There are approximately 600 naturally occurring carotenoids, but only six of these have so far been produced industrially. Insofar as applicants are aware, the only companies that manufacture synthetic "nature-identical" carotenoids at the present time are Roche (since 1954) and BASF (since 1960). Lycopene, a member of carotenoids, exhibits high radical scavenging ability and gives the health protection against a variety of serious disorders including cancer, heart disease, and degenerative eye diseases. Accordingly it has been widely used as an excellent additive in food, fodder and drugs. Indeed, chemists at Roche have developed an industrially feasible synthesis of lycopene characterized by Wittig condensation, but it requires the use of a very costly raw material triphenylphosphine. (See: K. Meyer, et al., Helv. Chim. Acta 1992, 75.1848.) Almost all early existing methods suffered from the use of triphenylphosphine.

A new synthesis method of lycopene (1) was reported in WO 0031086 by Babler et. al., in which diethyl 3,7,11-trimethyl-2,4,6,10-dodecatetraenylphosphonate (8) reacted with C10-dialdehyde (9) catalyzed by base to afford lycopene.

Thus lycopene can be prepared by the above four-step route starting with pseudoionone, in which 2,4,6,10-C15-tetraenylphosphonate (8) has been employed as the key intermediate and the triphenylphosphine discarded, and many improvement including a more simplified route has been observed compared with the known methods. But this new method still suffered from some limitations: the reagent C1P (OEt)2 is hard to prepare and sensitive to water and air; the costly NaBH4 and Pd/C is inevitably used as the hydrogenation reagent and catalyst; the selectivity of partial reduction is somewhat uncontrolled during the course of the conversion from allenic phosphonate compound (7) to allylic phosphonate (8) because of the competition between 1,2-allenic part and 4,5-double bond of phosphonate (7). So it is not suitable for industrial-scale production.

Recently, Shen et al has reported a new method for synthesis of lycopene (CN 201010189861.0), in which C14-acetal (2) was employed as the key intermediate:

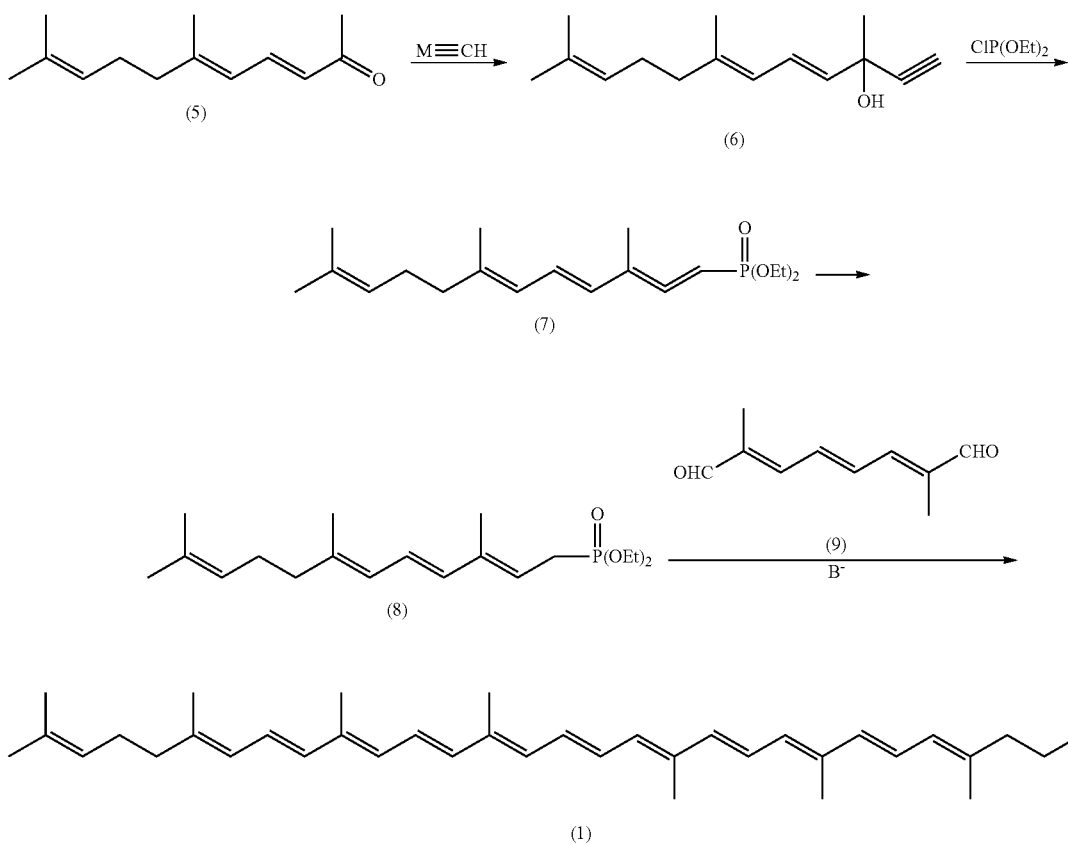

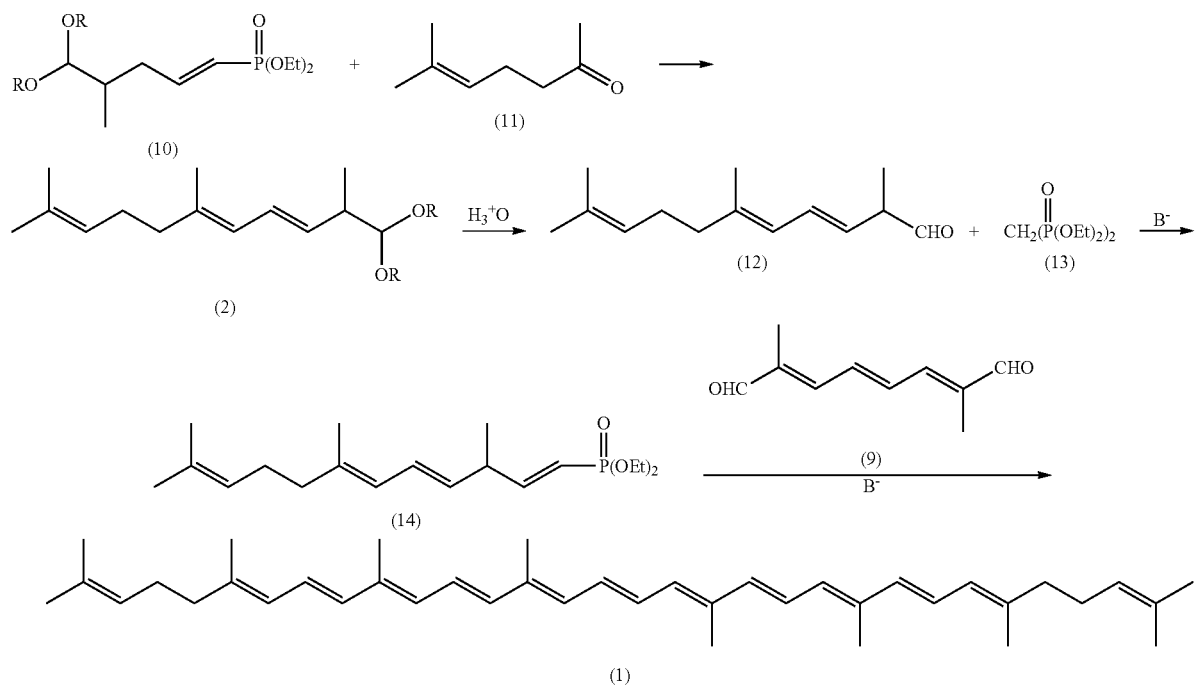

But this method still have some disadvantages that it is very difficult to gain the raw material dialkyl 4-methyl-5,5-dialkoxy-1-pentene-1-phosphonate (10) because no effective synthesis method can be adopted; furthermore, C14-acetal (2) prepared by this method is composed of several cis and trans isomers, which can't be converted to its all-trans form.

SUMMARY OF THE INVENTION

It is the objective of the present invention to reduce the disadvantage of the known process and to afford a method of preparing the intermediate C14-acetal (2) of lycopene which is characterized with simple procedure, easy access to raw material and low cost.

The method of preparing the intermediate 2,6,10-trimethyl-1,1-dialkoxy-3,5,9-Undecatriene of lycopene including the following steps:

1) Firstly, C10-phosphonate compound of formula (3) changed to its carbanion was carried out at a temperature of −40~30° C. under an atmosphere of a non-reactive gas (e.g., nitrogen gas) in an organic solvent catalyzed by base;

2) After the formation of the corresponding carbanion completely, C4-acetal of formula (4) was added to undergo Wittig-Horner condensation at a temperature of −40~30° C. under an atmosphere of a non-reactive gas (e.g., nitrogen gas) in an organic solvent catalyzed by base:

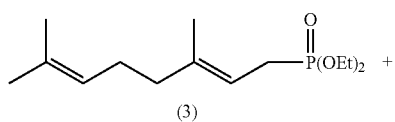

R=methyl or ethyl;

Followed by the completion of the above condensation, water and organic solvent were added and stratification. Then removal of the organic solvent afforded the target product all-trans-C14-acetal (2), and leave the by-product sodium diethyl phosphate dissolved in the aqueous layer.

During the process of the above condensation, the raw material C10-phosphonate (3) undergo dissociating to its corresponding carbanion catalyzed by a base firstly, and then C4-acetal (4) was added to finish the condensation, which can make the dissociation of C10-phosphonate (3) to its carbanion completely and is convenient to control the reaction.

The above raw material C4-acetal (4) is afforded by Zhejiang Medicine Co. Ltd., Xinchang Pharmaceutical Factory, also it can be prepared according to the literature (DE3403427, Verfahren zur Herstellung von 1,4-Butandial, 1985-01-08).

Suitable base in the reactions is alkali metal alkoxides or alkyllithium. Preferred base includes sodium ethoxide, sodium t-butoxide, potassium t-butoxide, n-Butyllithium and lithium diisopropylamide. There is no special restriction and other strong base can also be adopted.

Suitable molar ratio of C10-phosphonate (3) to base is 1:1.0~1.2, preferably molar ratio 1:1.02~1.1; molar ratio of C4-acetal (4) to C10-phosphonate (3) is 1:0.8~1.2, preferably molar ratio 1:0.9~1.0

Suitable solvent is ether or non-protonic solvent Preferably ether is dimethoxyethane, ether or THF, and non-protonic solvent is DMF, DMSO or HMPTA. Also the mixture of inert organic solvent and ether or non-protonic solvent can be used as the reaction solvent, and there is no special restriction for inert organic solvent, preferably alkyl hydrocarbon and aromatic hydrocarbon.

During the course of the above reaction, dissociation and condensation can be carried out at a preferable temperature of −20~10° C.

So this invention describes a method for the synthesis of the key intermediate C14-acetal (2) of lycopene starting from C10-phosphonate (3) and C4-acetal (4) only in one step of condensation. This method is characterized with the advantages of simple procedure, easy access to raw material and low cost, which makes it has the value of industrial application. Especially all trans C14-acetal can be obtained via Wittig-Horner condensation from all trans C10-phosphonate (3). The method provided in this invention is the only way to afford all trans C14-acetal (2) at the present time.

The invention will be illustrated by means of the following examples, without being limited thereto.

DETAILED DESCRIPTION OF THE INVENTION

The following examples are presented for purposes of illustration and should not be construed as limiting the invention which is delineated in the claims. Device and instrument used:

Example I

Preparation of diethyl (2E)-3,7-dimethyl-2,6-octdienylphosphonate (3A)

To a four-neck 1000 mL reaction flask with mechanical stirrer and thermometer 250 g of triethyl phosphite was added and heated to 150° C.-155° C., then a mixture of 172.7 g (E)-1-Chloro-3,7-dimethyl-2,6-octadiene and 160 g triethyl phosphite was added drop wise. The resulting mixture was stirred at 150° C.-155° C. for an additional 2 h to complete the reaction according to GC. Then cooling the mixture to room temperature, the excessive triethyl phosphite was recycled by vacuum distillation, and 272.8 g of distillate (105-109° C./1 mmHg) was collected as a light yellow transparent liquid with the content of 98.8% according to GC and the yield of 92.1%.

Identity of this compound was ascertained by NMR, IR and GC-MS analysis.

$^1$HNMR (400 MHz, CDCl$_3$) δ (ppm): 1.313 (t, J=7.2 Hz, 6H, 2OCH2CH*3); 1.602 (s, 3H, CH=C(CH*3)2); 1.656 (d, J=3.6 Hz, 3H, CH=CCH*3); 1.678 (s, 3H, CH=C(CH*3) 2); 2.030-2.099 (m, 4H, CH2CH2); 2.572 (dd, J=21.6 Hz, 7.6 Hz, 2H, CHCH*2P); 4.056-4.131 (m, 4H, 2OCH*2CH3); 5.069-5.103 (m, 1H, CH2CH*=CCH3); 5.168-5.222 (m, 1H, CH*=C(CH3)2).

$^{13}$CNMR (100 MHz, CDCl$_3$) δ (ppm): 15.975, 16.001; 16.201, 16.260; 17.389; 25.410; 26.169, 26.204; 26.802; 39.439, 39.467; 61.465, 61.532; 112.210, 112.320; 123.702; 131.200; 139.797, 139.941.

IR (v/cm−1): 1252, 1055, 1028, 792, 959.

GC-MS: 29, 41, 55, 67, 81 (100%), 93, 97, 111, 125, 138, 152, 163, 177, 191, 205, 219, 274.

Example II

Preparation of (all-E)-2,6,10-trimethyl-1,1-dimethoxyl-3,5,9-Undecatriene (2A)

A solution of 12.4 g of potassium t-butoxide (0.11 mol) in 60 mL of 8:1 (v/v) anhydrous tetrahydrofuran:dimethyl sulfoxide was added to a 500 mL three-neck reaction flask with mechanical stirrer under a nitrogen atmosphere in external cold bath. Then 29.2 g of diethyl (2E)-3,7-dimethyl-2,6-octadiene-phosphonate (3A) (0.10 mol) was added drop wise at −30~−25° C. over 0.5 h, and additional 1 h of stirring at this temperature was needed to accomplish the dissociation of 3A to its carbanion completely. Then 13.2 of 2-methyl-3,3-dimethoxy-1-propanal (4A) (0.10 mol) was added drop wise to the above reaction mixture at −30~−25° C. over 1 h and additional 0.5 h of stirring was needed to accomplish the reaction according to GC. Followed by the addition of 50 mL water and 100 mL ether and stirring for 10 min. After stratification, the organic layer was washed with 5% aqueous sodium chloride (3*25 mL), then dried over anhydrous magnesium sulfate and subsequently filtered. Removal of the volatile organic solvents in vacuo, the residue subsequently was fractional distillated to afford 18.4 g of (all-E)-2,6,10-trimethyl-1,1-dimethoxy-3,5,9-undecatriene (2A) (99-103° C./1 mmHg) as a colorless liquid with the content of 92.4% according to GC and the yield of 67.5%.

Identity of this compound was ascertained by NMR, DEPT135 and GC-MS analysis.

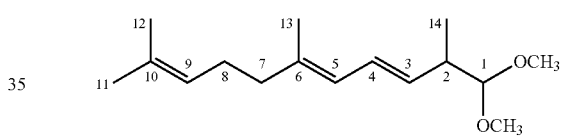

$^1$HNMR (δ ppm, 400 MHz, CDCl$_3$): 1.044 (d, J=6.8 Hz, 3H, C14-H); 1.603 (s, 3H, C12-H); 1.681 (s, 3H, C11-H); 1.745 (s, 3H, C13-H); 2.015-2.091 (m, 4H, C7-H, C8-H); 2.528-2.545 (m, 1H, C2-H); 3.359, 3.365 (s, s, 6H, (OCH3) 2); 4.089 (d, J=6.4 Hz, 1H, C1-H); 5.083-5.103 (m, 1H, C9-H); 5.535-5.593 (q, J=7.6 Hz, 1H, C3-H); 5.832 (d, J=10.8 Hz, 1H, C5-H); 6.295 (dd, J=10.8 Hz, 15.2 Hz, 1H, C4-H).

$^{13}$CNMR (δ ppm, 100 MHz, CDCl$_3$): 137.09 (C6); 132.42 (C3); 131.47 (C10); 126.85 (C4); 124.75 (C5); 124.11 (C9); 108.17 (C1); 54.12, 53.82 (OCH3); 39.90 (C7); 39.87 (C2); 26.59 (C8); 25.66 (C11); 17.63 (C12); 16.61 (C14); 15.43 (C13);

DEPT135: 132.42 (C3); 126.85 (C4); 124.75 (C5); 124.11 (C9); 108.17 (C1); 54.12, 53.82 (OCH3); 39.90 (C7, D); 39.87 (C2); 26.59 (C8, D); 25.66 (C11); 17.63 (C12); 16.61 (C14); 15.43 (C13);

GC-MS (m/z): 252, 220, 192 (100%), 178, 165, 152, 115, 102, 91, 77, 65, 51, 39.

Example III

Preparation of lycopene (1) from (all-E)-2,6,10-trimethyl-1,1-dimethoxyl-3,5,9-undecatriene (2A)

To a 250 mL four-neck reaction flask protected from atmospheric moisture by nitrogen gas throughout the course of the reaction a mixture of 12.6 g of (E)-2,6,10-trimethyl-1,1-dimethoxy-3,5,9-undecatriene (0.05 mol) of formula (2A), 100 mL THF and 1.2 g of PTSA was added. After stirred until homogeneous, 22 g of water was added, and additional 24 h of stirring at 20~25° C. was needed until the reaction completed according to GC. Then a solution of 2 g of NaHCO3 and 20 mL water was added for neutralization. After removal of THF by vacuum distillation, 100 mL of cyclohexane was added and then stratification. The organic layer was washed with 30 mL water, dried over anhydrous magnesium sulfate and subsequently filtered. Removal of the volatile organic solvents by evaporation at reduced pressure afforded 10.5 g of crude 2,6,10-trimethyl-3,5,9-undecatriene-1-aldehyde of formula (12).

To a 250 mL four-neck reaction flask protected from atmospheric moisture by nitrogen gas throughout the course of the reaction 2.2 g (0.055 mol) of sodium hydride (60% dispersion in mineral oil) was added, washed with hexane two times (20 mL per time) to remove the mineral oil, then 30 mL toluene was added and stirred to suspend sodium hydride. A solution of 17.2 g (0.06 mol) of methylenebisphosphonic acid tetramethyl ester in 50 mL toluene was added dropwise over 30 min, the reaction mixture maintained at a temperature of 10-15° C. by external cold water bath. This mixture was stirred for an additional 30 min, after which a solution of 10.5 g of crude 2,6,10-trimethyl-3,5,9-undecatrienyl-1-aldehyde (12) in 30 mL toluene was added dropwise over 30 min, the reaction mixture maintained at 10-15° C. by external cold water bath. This mixture was stirred for an additional 30 min, after which 50 mL water was added and stirred for 10 min. After stratification, the organic layer was washed with 10% aqueous sodium chloride (3*25 mL), then dried over anhydrous magnesium sulfate and subsequently filtered. Removal of the volatile organic solvents by evaporation at reduced pressure afforded 15.3 g of crude 1,4,6,10-tetraenyl-C15-phosphonate (14).

To a 250 mL four-neck reaction flask protected from atmospheric moisture by nitrogen gas throughout the course of the reaction a solution of 15.3 g (0.045 mol) of the above 1,4,6,10-tetraenyl-C15-phosphonate (14) in 50 mL of 8:1 (v/v) anhydrous tetrahydrofuran:dimethyl sulfoxide and 5.6 g (0.05 mol) of potassium tert-butoxide were added, and this mixture was stirred at a temperature of approximately 0° C. by use of an external cool bath for 2 h. Then a solution of 3.5 g (0.021 mol) of C10-dialdehyde (9) in 20 mL of 8:1 (v/v) anhydrous tetrahydrofuran:dimethyl sulfoxide was added dropwise over 1 h, and after additional 30 min stirring at 0° C., the mixture was warmed to 20-25° C. for further 1 h of stirring to accomplish the reaction. Then 250 mL of chloroform was added, and the mixture was washed with 5% aqueous sodium chloride (3*100 mL), removal of the volatile organic solvent in vacuo to leave the crude product, which can be further purified by recrystallization from dichloromethane to afford 6.8 g of lycopene.

The overall yield of the above three steps was 50.7%.

Identity of this compound was ascertained by NMR, DEPT135 and GC-MS analysis.

¹HNMR (δ ppm, 400 MHz, CDCl₃): δ 5.111, 5.975-6.943 (m, 8H, double-bond H), 5.11 (m, 1H), 1.552 (S, 6H), 1.616 (S, 3H), 1.689 (S, 3H), 2.129 (S, 3H), 1.427-2.212 (m, 4H)

¹³CNMR (100 MHz, CDCl₃) δ(ppm): 139.52 (C5); 137.37 (C12); 136.56 (C13); 136.19 (C9); 135.42 (C10); 132.66 (C14); 131.76 (C1); 131.58 (C8); 130.09 (C15); 125.73 (C11); 125.17 (C2); 124.82 (C6); 123.96 (C7); 40.25 (C4); 26.69 (C3); 25.72 (C20); 18.42 (C19); 16.97 (C18); 12.91 (C17); 12.81 (C16);

There are 13 peaks between δ (ppm) 120-140 and 7 peaks between δ (ppm) 10-45, which shows the high purity of all trans lycopene.

DEPT135: 137.37; 135.42; 132.66; 131.58; 130.09; 125.73; 125.17; 124.82; 123.96; 58.48 (D); 40.25 (D); 26.69 (D); 25.72; 18.42; 16.97; 12.91; 12.81.

Example IV

Preparation of (all-E)-2,6,10-trimethyl-1,1-diethoxy-3,5,9-undecatriene (2B)

To a 250 mL four-neck reaction flask protected from atmospheric moisture by nitrogen gas throughout the course of the reaction a solution of 12.4 g of potassium t-butoxide (0.11 mol) in 60 mL DMSO was added with an external cold bath to maintain the internal temperature of approximately −30 to −25° C. Then 29.2 g of diethyl(2E)-3,7-dimethyl-2,6-octadienyl-phosphonate (3A) (0.10 mol) was added dropwise over 30 min under stirring and the reaction mixture was subsequently stirred in the cold for 60 min to ensure the formation of carbanion thoroughly. Then 16.0 g of 2-methyl-3,3-diethoxy-1-propanal (4B) (0.10 mol) was added dropwise at −30~−25° C. over 1 h and the reaction mixture was subsequently stirred for 30 min at this temperature until the reaction completed according to GC. Followed by the addition of 30 mL water and 60 mL ether and stirring for 10 min, after stratification, the organic layer was washed with of 5% aqueous sodium chloride (3*25 mL), then dried over anhydrous magnesium sulfate and subsequently filtered. Removal of the volatile organic solvents in vacuo, the residue subsequently was fractional distillated to afford 21.0 g of (all-E)-2,6,10-trimethyl-1,1-diethoxy-3,5,9-undecatriene (2B) (99-103° C./1 mmHg) as a colorless liquid with GC content of 93.4% and the yield of 70.1%.

Identity of this compound was ascertained by NMR and DEPT135 analysis.

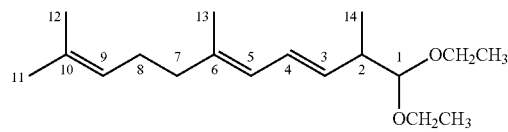

¹HNMR (δ ppm, 400 MHz, CDCl₃): 1.054 (d, J=6.8 Hz, 3H, C14-H); 1.194 (t, J=6.8 Hz, 6H, (OCH2CH*3)2); 1.604

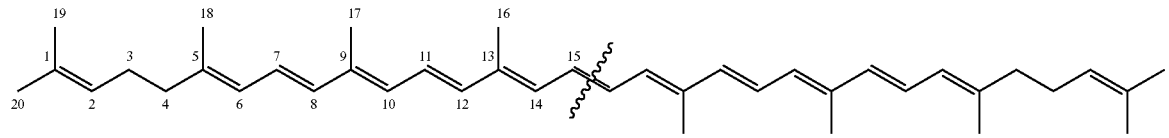

(s, 3H, C11-H); 1.680 (s, 3H, C12-H); 1.743 (s, 3H, C13-H); 2.038-2.108 (m, 4H, C7-H, C8-H); 2.506-2.523 (m, 1H, C2-H); 3.483-3.527, 3.640-3.700 (m, m, 4H, (OCH*2CH3)2); 4.213 (d, J=6.4 Hz, 1H, C1-H); 5.086-5.103 (m, 1H, C9-H); 5.560-5.617 (dd, J=7.6 Hz, 15.2 Hz, 1H, C3-H); 5.828 (d, J=10.8 Hz, 1H, C5-H); 6.284 (dd, J=10.8 Hz, 15.2 Hz, 1H, C4-H)

$^{13}$CNMR ($\delta$ ppm, 100 MHz, CDCl$_3$): 136.77 (C6); 132.85 (C3); 131.41 (C10); 126.71 (C4); 124.88 (C5); 124.10 (C9); 106.24 (C1); 62.18, 62.10 (OCH*2CH3); 40.57 (C2); 39.87 (C7); 26.58 (C8); 25.63 (C11); 17.61 (C14); 16.56 (C12); 15.32 (C13); 15.25 (OCH2CH*3)

DEPT135: 132.85; 126.71; 124.88; 124.10; 106.24; 62.18, 62.10 (D); 40.57; 39.87 (D); 26.58 (D); 25.63; 17.61; 16.56; 15.32; 15.25.

Example V

Preparation of lycopene (1) from (all-E)-2,6,10-trimethyl-1,1-diethoxy-3,5,9-Undecatriene (2B)

To a 250 mL four-neck reaction flask protected from atmospheric moisture by nitrogen gas throughout the course of the reaction a solution of 14.0 g of (all-E)-2,6,10-trimethyl-1,1-diethoxy-3,5,9-undecatriene (0.05 mol) of formula (2B), 100 mL tetrahydrofuran and 1.2 g of PTSA was added, Followed by stirring until homogeneous, 22 g of water was added, and an additional 24 h of stirring at 20~25° C. was needed until the reaction completed according to GC. Then a solution of 2 g of NaHCO3 and 20 mL water was added for neutralization. Removal of THF by vacuum distillation, 100 mL cyclohexane was added and then stratification. The organic layer was washed with 30 mL water, dried over anhydrous magnesium sulfate and subsequently filtered. Removal of the volatile organic solvents by evaporation at reduced pressure afforded 10.3 g of crude 2,6,10-trimethyl-3,5,9-undecatrienyl-1-aldehyde of formula (12).

To a 250 mL four-neck reaction flask protected from atmospheric moisture by nitrogen gas throughout the course of the reaction 2.2 g (0.055 mol) of sodium hydride (60% dispersion in mineral oil) was added, washed with hexane two times (20 mL per time) to remove the mineral oil, and then 30 mL of toluene was added and stirred to suspend sodium hydride. Then a solution of 17.2 g (0.06 mol) of methylenebisphosphonic acid tetramethyl ester in 50 mL toluene was added dropwise over 30 min, the reaction mixture maintained at a temperature of 10-15° C. by external cold water bath. This mixture was stirred for an additional 30 min, after which a solution of 10.3 g of crude 2,6,10-trimethyl-3,5,9-undecatrienyl-1-aldehyde of formula (12) in 30 mL toluene was added dropwise over 30 min, the reaction mixture maintained at 10-15° C. by external cold water bath. The resulting mixture was stirred for an additional 30 min, after which 50 mL water was added and stirred for 10 min. After stratification, the organic layer was washed with 10% aqueous sodium chloride (3*25 mL), then dried over anhydrous magnesium sulfate and subsequently filtered. Removal of the volatile organic solvents by evaporation at reduced pressure afforded 15.0 g of crude 1,4,6,10-tetraenyl-C15-phosphonate (14).

To a 250 mL four-neck reaction flask protected from atmospheric moisture by nitrogen gas throughout the course of the reaction a solution of 15.0 g of the above 1,4,6,10-tetraenyl-C15-phosphonate (14) in 50 mL of 8:1 (v/v) anhydrous tetrahydrofuran:dimethyl sulfoxide and 5.6 g (0.05 mol) of potassium tert-butoxide were added, and this mixture was stirred at a temperature of approximately 0° C. by use of an external cool bath for 2 h. Then a solution of 3.5 g of (0.021 mol) of C10-dialdehyde in 20 mL of 8:1 (v/v) anhydrous tetrahydrofuran:dimethyl sulfoxide was added dropwise over 1 h, and after an additional 30 min stirring at 0° C., the mixture was warmed to 20-25° C. for further 1 h of stirring to accomplish the reaction. Then 250 mL of chloroform was added, and the mixture was washed with 5% aqueous sodium chloride (3*100 mL), removal of the volatile organic solvent in vacuo to leave the crude product, which can be further purified by recrystallization from dichloromethane to afford 6.5 g of lycopene.

The overall yield of the above three steps was 48.4%. Identity of this compound was ascertained by CNMR. and is the same with that of Example III.

Example VI

Preparation of the mixture of diethyl (2E and 2Z)-3,7-dimethyl-2,6-octdienylphosphonate (3B)

To a 500 mL four-neck reaction flask with mechanical stirrer and thermometer, 125 g of triethyl phosphite was added and heated to 150° C.-155° C., then a mixture of 86.3 g of (2E and 2Z)-1-chloro-3,7-dimethyl-2,6-octadiene and 80 g of triethyl phosphite was added. Further 2 h was needed to finish the reaction according to GC. After cooling the mixture to room temperature, the unreacted triethyl phosphite was recycled by vacuum distillation, and the residue evaporated in vacuo, 137.5 g of distillate of 105-109° C./1 mmHg was collected as a light yellow transparent liquid with the content of 97.6% (total content of cis and trans s) according to GC and the yield of 91.7%.

Example VII

Preparation of the mixture of (5E and 5Z)-2,6,10-trimethyl-1,1-dimethoxy-3,5,9-undecatriene (2C)

To a 500 mL three-neck reaction flask protected from atmospheric moisture by nitrogen gas throughout the course of the reaction a solution of 2.4 g potassium t-butoxide (0.11 mol) in 60 mL of anhydrous tetrahydrofuran was added with an external cold bath to maintain the internal temperature of approximately −30 to −25° C. Then diethyl 3,7-dimethyl-2,6-octadiene-phosphonate (3B) (0.10 mol) was added dropwise over 30 min under mechanical stirring and the reaction mixture was subsequently stirred in the cold for 60 min to ensure the formation of carbanion thoroughly. Then 13.2 g of 2-methyl-3,3-dimethoxy-1-propanal (4A) (0.10 mol) was added dropwise at −30~25° C. over 1 h and the reaction mixture was subsequently stirred for 30 min at this temperature until the reaction completed according to GC. Followed by the addition of 50 mL water and 100 mL ether and stirring for 10 min, after stratification, the organic layer was washed with 5% aqueous sodium chloride (3×25 mL), then dried over anhydrous magnesium sulfate and subsequently filtered. Removal of the volatile organic solvents in vacuo, the residue subsequently was fractional distillated to afford 17.9 g of (5-E and 5-Z)-2,6,10-trimethyl-1,1-dimethoxy-3,5,9-undecatriene (2C) of 99-103° C./1 mmHg, as a colorless liquid with GC content of 92.5% (total content of cis and trans) and the yield of 65.7%. There are 2 peaks according to GC and GC-MS. ascertained is the same with that of Example II

Example VIII

Preparation of lycopene (1) from the mixture of (5E- and 5Z)-2,6,10-trimethyl-1,1-dimethoxy-3,5,9-undecatriene (2C)

To a 250 mL four-neck reaction flask protected from atmospheric moisture by nitrogen gas throughout the course of the reaction a solution of 12.6 g in 2,6,10-trimethyl-1,1-dimethoxy-3,5,9-undecatriene (2C, 0.05 mol), 100 mL tetrahydrofuran and 1.2 g of PTSA was added. After stirred until homogeneous, 22 g of water was added, and further 24 h of stirring at 20-25° C. was needed until the reaction completed according to GC. Then a solution of 2 g of NaHCO3 in 20 mL water was added for neutralization. Removal of THF by vacuum distillation, 100 mL of cyclohexane was added and then stratification. The organic layer was washed with 30 mL of water, dried over anhydrous magnesium sulfate and subsequently filtered. Removal of the volatile organic solvents by evaporation at reduced pressure afforded 10.5 g of crude 2,6,10-trimethyl-3,5,9-undecatriene-1-aldehyde of formula (12).

To a 250 mL four-neck reaction flask protected from atmospheric moisture by nitrogen gas throughout the course of the reaction 2.2 g (0.055 mol) of sodium hydride (60% dispersion in mineral oil) was added, washed with hexane two times (20 mL per time) to remove the mineral oil, and then 30 mL of toluene was added and stirred to suspend sodium hydride. Then a solution of 17.2 g (0.06 mol) of methylenebisphosphonic acid tetramethyl ester in 50 mL toluene was added dropwise over 30 min, the reaction mixture maintained at a temperature of 10-15° C. by external cold water bath. This mixture was stirred for an additional 30 min, after which a solution of 10.5 g of crude 2,6,10-trimethyl-3,5,9-undecatriene-1-aldehyde of formula (12) in 30 mL toluene was added dropwise over 30 min, the reaction mixture maintained at 10-15° C. by external cold water bath. This mixture was stirred for an additional 30 min, after which 50 mL water was added and stirred for 10 min. After stratification, the organic layer was washed with 5% aqueous sodium chloride (3*25 mL), then dried over anhydrous magnesium sulfate and subsequently filtered. Removal of the volatile organic solvents by evaporation at reduced pressure afforded 15.3 g of crude 1,4,6,10-tetraenyl-C15-phosphonate (14).

To a 250 mL four-neck reaction flask protected from atmospheric moisture by nitrogen gas throughout the course of the reaction a solution of 15.3 g (0.045 mol) of the above 1,4,6,10-tetraenyl-C15-phosphonate (14) in 50 mL of 8:1 (v/v) anhydrous tetrahydrofuran:dimethyl sulfoxide and 5.6 g (0.05 mol) of potassium tert-butoxide were added, and this mixture was stirred at a temperature of approximately 0° C. by use of an external cool bath for 2 h. Then a solution of 3.5 g (0.021 mol) of C10-dialdehyde in 20 mL of 8:1 (v/v) anhydrous tetrahydrofuran:dimethyl sulfoxide was added dropwise over 1 h, and after an additional 30 min stirring at 0° C., the mixture was warmed to 20-25° C. for further 1 h of stirring to accomplish the reaction. Then 250 mL of chloroform was added, and the mixture was washed with 5% aqueous sodium chloride (3*100 mL) and subsequently filtered. The filtrate was refluxed under nitrogen atmosphere for 3 h. Then removal of the volatile organic solvent in vacuo to leave the crude product, which can be further purified by recrystallization from dichloromethane to afford 6.6 g of lycopene.

The overall yield of the above three steps was 49.2%. Identity of this compound was ascertained by CNMR. and is the same with that of Example III.

Example IX

Preparation of the mixture of (5-E and 5-Z)-2,6,10-trimethyl-1,1-diethoxy-3,5,9-undecatriene (2D)

To a 500 mL three-neck reaction flask protected from atmospheric moisture by nitrogen gas throughout the course of the reaction a solution of 2.4 g potassium tert-butoxide (0.11 mol) in 60 mL of anhydrous tetrahydrofuran was added. Then 29.2 g of diethyl 3,7-dimethyl-2,6-octadienyl-phosphonate (3B) (0.10 mol) was added dropwise over 30 min under mechanical stirring by use of an external cold bath to maintain the internal temperature of approximately −30 to −25° C., and the reaction mixture was subsequently stirred in the cold for 60 min to ensure the formation of carbanion thoroughly. Then 16 g of 2-methyl-3,3-diethoxy-1-propanal (4B) (0.10 mol)) was added dropwise at −30~−25° C. over 1 h and the reaction mixture was subsequently stirred for 30 min at this temperature until the reaction completed according to GC. Followed by the addition of 50 mL water and 100 mL ether and stirring for 10 min, after stratification, the organic layer was washed with 5% aqueous sodium chloride (3×25 mL), then dried over anhydrous magnesium sulfate and subsequently filtered. Removal of the volatile organic solvents in vacuo, the residue subsequently was fractional distillated to afford 19.7 g of (5-E and 5-Z)-2,6,10-trimethyl-1,1-diethoxy-3,5,9-undecatriene (2D) of 99-103° C./1 mmHg, as a colorless liquid with GC content of 94.2% (total content of cis and trans) and the yield of 66.3%. There are 2 peaks according to GC and GC-MS. ascertained is the same with that of Example IV Example X Preparation of lycopene (1) from the mixture of (5-E and 5-Z)-2,6,10-trimethyl-1,1-diethoxy-3,5,9-undecatriene (2D)

To a 250 mL four-neck reaction flask protected from atmospheric moisture by nitrogen gas throughout the course of the reaction a solution of 14.0 g 2,6,10-trimethyl-1,1-diethoxy-3,5,9-undecatriene (2D, 0.05 mol), 100 mL tetrahydrofuran and 1.2 g of PTSA was added. After stirred until homogeneous, 22 g of water was added, and further 24 h of stirring at 20-25° C. was needed until the reaction completed according to GC. Then a solution of 2 g of NaHCO3 in 20 mL water was added for neutralization. Removal of THF by vacuum distillation, 100 mL of cyclohexane was added and then stratification. The organic layer was washed with 30 mL of water, dried over anhydrous magnesium sulfate and subsequently filtered. Removal of the volatile organic solvents by evaporation at reduced pressure afforded 10.3 g of crude 2,6,10-trimethyl-3,5,9-undecatriene-1-aldehyde of formula (12).

To a 250 mL four-neck reaction flask protected from atmospheric moisture by nitrogen gas throughout the course of the reaction 2.2 g (0.055 mol) of sodium hydride (60% dispersion in mineral oil) was added, washed with hexane two times (20 mL per time) to remove the mineral oil, and then 30 mL of toluene was added and stirred to suspend sodium hydride. Then a solution of 17.2 g (0.06 mol) of methylenebisphosphonic acid tetramethyl ester in 50 mL toluene was added dropwise over 30 min, the reaction mixture maintained at a temperature of 10-15° C. by external cold water bath. This mixture was stirred for an additional 30 min, after which a solution of 10.3 g of crude 2,6,10-trimethyl-3,5,9-undecatriene-1-aldehyde of formula (12) in 30 mL toluene was added dropwise over 30 min, the reaction mixture maintained at 10-15° C. by external cold water bath. This mixture was stirred for an additional 30 min, after which 50 mL water was added and stirred for 10 min. After stratification, the organic layer was washed with 5% aqueous sodium chloride (3*25 mL), then dried over anhydrous magnesium sulfate and subsequently filtered. Removal of the volatile organic solvents by evaporation at reduced pressure afforded 15.0 g of crude 1,4,6,10-tetraenyl-C15-phosphonate (14).

To a 250 mL four-neck reaction flask protected from atmospheric moisture by nitrogen gas throughout the course of the reaction a solution of 15.0 g of the above 1,4,6,10-tetraenyl-C15-phosphonate (14) in 50 mL of 8:1 (v/v) anhydrous tetrahydrofuran:dimethyl sulfoxide and 5.6 g (0.05 mol) of potassium tert-butoxide were added, and this mixture was stirred at a temperature of approximately 0° C. by use of an external cool bath for 2 h. Then a solution of 3.5 g (0.021 mol) of C10-dialdehyde (0.021 mol) in 20 mL of 8:1 (v/v) anhydrous tetrahydrofuran:dimethyl sulfoxide was added dropwise over 1 h, and after an additional 30 min stirring at 0° C., the mixture was warmed to 20-25° C. for further 1 h of stirring to accomplish the reaction. Then 250 mL of chloroform was added, and the mixture was washed with 5% aqueous sodium chloride (3*100 mL) and subsequently filtered. The filtrate was refluxed under nitrogen atmosphere for 3 h. Then removal of the volatile organic solvent in vacuo to leave the crude product, which can be further purified by recrystallization from dichloromethane to afford 6.6 g of lycopene.

The overall yield of the above three steps was 49.2%. Identity of this compound was ascertained by CNMR. and is the same with that of Example III.

Example XI-XVI

Preparation of (all-E)-2,6,10-trimethyl-1,1-dimethyl-3,5,9-undecatriene (2A) in Different Reaction Conditions of Base, Solvent and Temperature To a 250 mL 3-neck reaction flask protected from atmospheric moisture by nitrogen gas throughout the course of the reaction, base and 60 mL solvent was added (see table 1), a solution of diethyl (2E)-3,7-dimethyl-2,6-octadienyl-phosphonate (3A) (dosage see table 1) in 40 mL solvent (the same as above) was added dropwise over 30 min, the reaction mixture maintained at a certain degree (see table 1), and the reaction mixture was subsequently stirred in the cold for 60 min to ensure the formation of carbanion thoroughly.

Then 13.2 g of 2-methyl-3,3-dimethoxy-1-propanal (4A) (0.10 mol)) was added dropwise at the above given temperature over 1 h and the reaction mixture was subsequently stirred for 30 min at this temperature until the reaction completed according to GC. Followed by the addition of 50 mL water and 100 mL ether and stirring for 10 min, after stratification, the organic layer was washed with 5% aqueous sodium chloride (3×25 mL), then dried over anhydrous magnesium sulfate and subsequently filtered. Removal of the volatile organic solvents in vacuo, the residue subsequently was fractional distillated to afford (all-E)-2,6,10-trimethyl-1,1-dimethoxy-3,5,9-undecatriene (2A) of 99-103° C./1 mmHg, as a colorless liquid. The content checked by G. C., and yield calculated see the table below.

TABLE 1

| EXAMPLE | Base | Dosage of base (mol) | solvent | 3A (g, mol) | Reaction temperature (° C.) | Product (g) | Content (%) | Yield (%) |
|---|---|---|---|---|---|---|---|---|
| 11 | Sodium ethoxide | 0.12 | DMF | 29.2, 0.10 | 30 | 12.6 | 86.2 | 43.1 |
| 12 | Sodium t-butoxide | 0.10 | dimethoxyethane | 26.3, 0.09 | −10 | 16.4 | 87.5 | 56.9 |
| 13 | n-Butyllithium | 0.10 | THF/ n-hexane | 27.7, 0.095 | −40 | 19.6 | 91.6 | 71.2 |
| 14 | potassium t-butoxide | 0.13 | DMSO | 38.0, 0.13 | −20 | 17.8 | 90.7 | 64.1 |
| 15 | lithium diisopropylamide | 0.114 | Hexamethylphosphoric triamide | 32.7, 0.112 | 10 | 19.4 | 91.4 | 70.5 |
| 16 | Sodium t-butoxide | 0.92 | Hexamethylphosphoric triamide | 24.5, 0.84 | 0 | 17.8 | 89.3 | 62.4 |

What is claimed is:

1. A method of preparing 2,6,10-trimethyl-1,1-dialkoxy-3,5,9-undecatriene (2) used as an intermediate of lycopene Comprising the steps:
  1) Firstly, C10-phosphonate compound of formula (3) changed to its carbanion was carried out at a temperature of −40~30° C. under an atmosphere of a non-reactive gas in an organic solvent catalyzed by base;
  2) After the formation of the corresponding carbanion completely, C4-acetal of formula (4) was added to undergo Wittig-Horner condensation at a temperature of −40~30° C. under an atmosphere of a non-reactive gas in an organic solvent catalyzed by base:

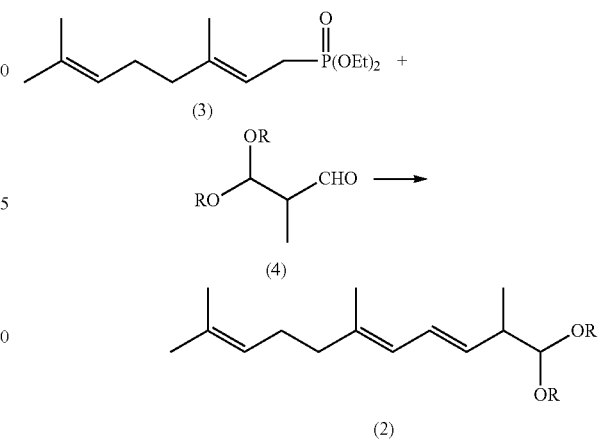

R=methyl or ethyl;
Followed by the completion of the above condensation, water and organic solvent is added and stratified, Then removal of the organic solvent afforded the target product all trans C14-acetal of formula (2), and leave the by-product sodium diethyl phosphate dissolved in the aqueous layer.

2. The method of claim 1, wherein the suitable solvent is ether, non-protonic solvent or the mixture of ether or non-protonic solvent and inert organic solvent.

3. The method of claim 2, wherein said ether is dimethoxyethane, ether or THF.

4. The method of claim 2, wherein said non-protonic solvent is DMF, DMSO or HMPTA.

5. The method of claim 2, wherein said inert organic solvent is alkyl hydrocarbon or aromatic hydrocarbon.

6. The method of claim 2 wherein said molar ratio of C10-phosphonate (3) to base is 1:1.0~1.2; molar ratio of C4-acetal (4) to C10-phosphonate (3) is 1:0.8~1.2.

7. The method of claim 6, wherein said molar ratio of C10-phosphonate (3) to base is 1:1.02~1.1; molar ratio of C4-acetal (4) to C10-phosphonate (3) is 1:0.9~1.0.

8. The method of claim 2, wherein said base are alkali metal alkoxides or alkyllithium.

9. The method of claim 8, wherein said suitable base is sodium ethoxide, sodium t-butoxide, potassium t-butoxide, n-Butyllithium.

10. The method of claim 2, wherein said suitable reaction temperatures from approximately −20~10° C.

* * * * *